| United States Patent [19]
Shimizu et al.

[11] Patent Number: 5,008,445
[45] Date of Patent: Apr. 16, 1991

[54] PROCESS FOR THE PRODUCTION OF GLYCOL MONOESTERS

[75] Inventors: Nobuaki Shimizu; Hiroaki Kezuka, both of Sodegaura, Japan

[73] Assignee: Idemitsu Kosan Company Limited, Tokyo, Japan

[21] Appl. No.: 59,153

[22] Filed: Jun. 5, 1987

Related U.S. Application Data

[63] Continuation of Ser. No. 821,690, Jan. 23, 1986, abandoned, Continuation-in-part of Ser. No. 698,319, Feb. 5, 1985, abandoned.

[30] Foreign Application Priority Data

Feb. 10, 1984 [JP] Japan .................................. 59-24127
Dec. 12, 1984 [JP] Japan ................................ 59-260790

[51] Int. Cl.$^5$ .................... C07C 67/055; C07C 69/16; C07C 69/28
[52] U.S. Cl. ...................... 560/243; 502/24; 502/53; 560/263
[58] Field of Search ................ 560/243, 263; 502/53, 502/22, 24, 28

[56] References Cited

U.S. PATENT DOCUMENTS 3,210,152 10/1965 van Helden et al. ............... 560/243
3,859,336 1/1975 Aguilo et al. ....................... 560/243
4,052,442 10/1977 Tamura et al. ..................... 560/243

OTHER PUBLICATIONS

Phillips, F. C., Amer. Chem. Jour., 16, 255, 1894.

*Primary Examiner*—Vivian Garner
*Attorney, Agent, or Firm*—Frishauf, Holtz, Goodman & Woodward

[57] ABSTRACT

The present invention relates to a process for producing glycol monoesters by reacting carboxylic acid, olefin and oxygen in the presence of a catalyst containing (A) a palladium component, (B) an oxygen-containing nitrogen compound, and (C) a metal halide in the specified ratio of (A), (B), (C).

According to the present invention, the regeneration of the catalyst through reduction is easy and the catalyst of high activity can be used repeatedly.

26 Claims, No Drawings

PROCESS FOR THE PRODUCTION OF GLYCOL MONOESTERS

CROSS REFERENCE TO OTHER APPLICATION

This application is a continuation of application Ser. No. 821,690, filed Jan. 23, 1986, now abandoned, which is a continuation-in-part of application Ser. No. 698,319, filed Feb. 5, 1985, now abandoned.

BACKGROUND OF THE INVENTION

The present invention relates to a process for the production of glycol monoesters. More particularly, it relates to a process for efficiently producing glycol monoesters by reacting carboxylic acids, olefins, and oxygen in the presence of a specific catalyst.

It is known as described in Japanese Patent Publication No. 32413/1970 and Japanese Patent Application Laid-Open No. 82213/1976, for example, that glycol esters are produced by reacting carboxylic acids, olefins, and oxygen in the presence of a catalyst comprising a palladium component, an oxygen-containing nitrogen compound, and a metal halide.

Such conventional catalysts, however, have a disadvantage in that although their activity is sufficiently high at the beginning of a reaction, it seriously drops in several hours after the start of the reaction, and even if the catalysts are regenerated by reduction, their original activity is difficult to recover sufficiently.

SUMMARY OF THE INVENTION

The present invention is intended to overcome the above-described problem of the conventional palladium catalysts, and an object of the present invention is to provide an improved process for the production of glycol monoesters in which a drop in activity of the catalyst is minimized. It has been found that the object is attained by specifying the proportion of the oxygen-containing nitrogen compound in the catalyst.

The present invention relates to a process for producing glycol monoesters by reacting at least one carboxylic acid selected from the group consisting of acetic acid, propionic acid, butyric acid and isobutyric acid, at least one olefin selected from the group consisting of ethylene, propylene, butene-1, butene-2, cyclopentene and cyclohexene, and oxygen in the presence of a catalyst containing (A) a palladium component, (B) an oxygen-containing nitrogen compound and (C) a metal halide as major constituents, wherein the molar ratio of the oxygen-containing nitrogen compound (B) to the palladium component (A) is from 0.5 to less than 2.0 and the elemental ratio of the halogen atom in the metal halide (C) to the palladium atom in the palladium component (A) is 1 or more.

DETAILED DESCRIPTION OF THE INVENTION

The catalyst for use in the process of the present invention comprises the above-described components (A), (B), and (C).

Suitable as the palladium component (A) is metallic palladium. In addition, palladium compounds can be used, including palladium salts such as sodium palladium chloride, palladium nitrate, palladium acetate, palladium chloride, and palladium bromide, and palladium oxides. Although it is preferred for the palladium component to be used as it is, it may be deposited on a carrier. There is no special limitation on the amount of the palladium component (A) used; usually it is sufficient that the concentration of the palladium component (A) in the reaction system is in the range of from 0.001 to 0.1 mole per liter.

The oxygen-containing nitrogen compound (B) includes nitric acid, nitrogen monoxide, nitrogen dioxide, nitrous acid esters, nitric acid salts such as lithium nitrate and sodium nitrate, and nitrous acid salts such as copper nitrite, lithium nitrite, and sodium nitrite. The oxygen-containing nitrogen compound (B) is used in such an amount that the molar ratio of the oxygen-containing nitrogen compound (B) to the palladium component (A) is from 0.5 to less than 2, preferably from 0.5 to 1.5. If the molar ratio of the oxygen-containing nitrogen compound (B) to the palladium component (A) is in excess of 2, although the initial activity of the catalyst is increased, its activity seriously drops when reused after regeneration; therefore, the catalyst is unsuitable for practical use.

The metal halide (C) includes lithium chloride, sodium chloride, copper chloride, manganese chloride, zinc chloride, cobalt chloride, bismuth chloride and antimony chloride.

The elemental ratio of the halogen atom in the metal halide (C) to the palladium atom in the palladium component (A) is at least 1 and preferably from 1 to 3. Outside this range, the conversion to glycol esters is undesirably decreased. In a case that the palladium component (A) contains halogen, it is possible to reduce the amount of the metal halide (C) added.

In the process of the present invention, at least one carboxylic acid selected from the group consisting of acetic acid, propionic acid, butyric acid and isobutyric acid, at least one olefin selected from the group consisting of ethylene, propylene, butene-1, butene-2, cyclopentene and cyclohexene, and oxygen are reacted in the presence of the catalyst containing the above components (A), (B) and (C) as major constituents. Oxygen is not limited to pure oxygen gas, and air, for example, can also be used. In addition, mixed gases of oxygen and other gases such as nitrogen, carbon dioxide, methane, ethene, propane, and butene can be used.

There is no special limitation to the amounts of the carboxylic acid, olefin, and oxygen to be used. The molar ratio of olefin to oxygen is preferably from 1.8 to 2.2. If the amount of oxygen used is too large, there is a danger of explosion. On the other hand, if the amount of the olefin is too large, the conversion is undesirably low.

The reaction among the carboxylic acid, olefin, and oxygen can be carried out under various conditions. Usually the temperature is chosen appropriately within the range of from 15° to 120° C., preferably from 40° to 80° C.; the pressure, within the range of from atmospheric pressure to superatmospheric pressure; and the time, within the range of from 1 to 5 hours.

After the reaction proceeds to a certain extent, nitrogen gas, for example, is introduced into the reaction system to stop the reaction. Then, hydrogen gas is introduced into the reaction system at a temperature of from 20° to 150° C., preferably from 50° to 80° C. under a pressure of from atmospheric pressure to 10 kilograms per square meter (by gauge), preferably near atmospheric pressure, and the palladium component (A) is reduced with hydrogen for from about 0.1 to 1 hour. In this case, it is desirable that the reaction be stopped when the amount of the offgas nearly exceeds 10% of the charged amount of the hydrogen and, thereafter, the hydrogen reduction be carried out. The above regeneration process enables rapid and sufficient recovery of the original activity of the palladium component (A).

In the present invention, as described above, the regeneration of the catalyst through reduction is easy and the catalyst of high activity can be used repeatedly since the oxygen-containing nitrogen component (B) is used in the above-specified amount relative to the palladium component (A).

The process of the present invention enables production of glycol monoesters such as ethylene glycol monoesters, and propylene glycol monoesters that are useful as intermediates, with high efficiency while greatly lengthening the service life of the catalyst through the regeneration thereof.

The present invention is described in greater detail with reference to the following examples.

EXAMPLE 1

A 100-milliliter four-necked flask equipped with a stirrer, a cooler, and a gas-introduction tube was charged with 1 millimole of metallic palladium, 1 millimole of lithium nitrate, 2 millimoles of lithium chloride, and 60 milliliters of acetic acid, which were then vigorously stirred while heating on an oil bath maintained at 60° C. After 5 minutes, ethylene and oxygen were introduced into the flask at rates of 12 milliliters per minute and 6 milliliters per minute, respectively. All the ethylene and oxygen introduced were consumed and no waste gas was formed. After four hours from the start of the reaction, the introduction of the ethylene and oxygen was stopped and nitrogen gas was introduced into the flask to replace the ethylene and oxygen therewith. Then, hydrogen gas was introduced into the flask at a rate of 20 milliliters per minute for 20 minutes to regenerate the deteriorated catalyst. Subsequently, nitrogen gas was again introduced into the flask to remove hydrogen, and only a liquid was taken out of the flask. To the regenerated palladium remaining in the flask were added 1 millimole of lithium nitrate, 2 millimoles of lithium chloride, and 60 milliliters of acetic acid. Thereafter, in the same manner as above, ethylene and oxygen were introduced into the flask to perform the second reaction.

The above procedure of from reaction to regeneration of catalyst was repeated 30 times. Reaction products as obtained at each reaction were analyzed, and the results at the first, 15th, and 30th reactions are shown in Table 1.

After the 30th regeneration, X-ray photoelectric spectral and infrared absorption spectral analyses of the regenerated palladium were conducted. These analyses showed that there was not any deactivated catalyst $(Pd(CN)_2)$.

EXAMPLE 2

The procedure of Example 1 was repeated wherein ethylene was replaced with propylene and the reaction time was changed to 3 hours. The results of the reaction are shown in Table 2.

After the 30th regeneration, the X-ray photoelectric spectral and infrared absorption spectral analyses of the regenerated palladium were conducted. These analyses showed that there was not any deactivated catalyst $(Pd(CN)_2)$.

COMPARATIVE EXAMPLE 1

The same reaction and catalyst regeneration operation as in Example 2 was repeated 20 times wherein the amount of lithium nitrate was changed to 4 millimoles. At and after the third reaction, the formation of yellow fine powder in the reaction mixture was observed. At the 9th reaction, the formation of unreacted gas was observed. The results of the reaction are shown in Table 3. After the 20th regeneration, the X-ray photoelectric spectral and infrared absorption spectral analyses of the regenerated palladium were conducted. These analyses showed that there was a considerable amount of deactivated catalyst.

COMPARATIVE EXAMPLE 2

The same reaction and catalyst regeneration operation as in Example 2 was repeated 3 times wherein the amount of lithium nitrate was changed to 15 millimoles. At the third reaction, the conversion of propylene seriously dropped. For this reason, the 4th and subsequent reactions were not conducted. The results are shown in Table 4. After the third regeneration, the X-ray photoelectric spectral and infrared absorption spectral analyses of the palladium component obtained were conducted. These analyses showed that almost all the catalyst was deactivated.

EXAMPLE 3

The procedure of Example 2 was repeated wherein lithium nitrate was replaced with normal butyl nitrite and the reaction time was changed to 5 hours.

The results at the first reaction are shown in Table 5.

EXAMPLE 4

The procedure of Example 2 was repeated wherein lithium nitrate was replaced with sodium nitrite and the reaction time was changed to 2 hours.

The results at the first reaction are shown in Table 5.

EXAMPLES 5 to 10

The procedure of Example 2 was repeated except that the amount of lithium nitrate was changed to 1.5 millimoles and that the type and amount of metal halide were changed as shown in Table 6 inplace of lithium chloride.

The results at the first reaction are shown in Table 6.

TABLE 1

|  | First Reaction | 15th Reaction | 30th Reaction |
|---|---|---|---|
| Reaction Products (millimoles) | | | |
| Ethylene glycol monoacetate | 90.1 | 80.5 | 82.3 |
| Ethylene glycol diacetate | 2.0 | 2.1 | 2.3 |
| Acetaldehyde | 8.5 | 8.4 | 8.2 |
| Ethylidene diacetate | 17.1 | 16.6 | 16.1 |
| Conversion (%) | 91.5 | 83.7 | 84.7 |
| Selectivity (%)* | 78.2 | 76.8 | 77.7 |

Note:
*Selectivity of the sum of ethylene glycol monoacetate and ethylene glycol diacetate

TABLE 2

|  | First Reaction | 15th Reaction | 30th Reaction |
|---|---|---|---|
| Reaction Products (millimoles) | | | |
| Propylene glycol monoacetate | 65.3 | 60.4 | 60.3 |
| Propylene glycol diacetate | 2.8 | 2.2 | 2.5 |

TABLE 2-continued

|  | First Reaction | 15th Reaction | 30th Reaction |
|---|---|---|---|
| Propionaldehyde and acetone | 17.9 | 14.6 | 17.4 |
| Conversion (%) | 89.2 | 80.1 | 83.2 |
| Selectivity (%)** | 79.2 | 81.1 | 78.3 |

Note:
**Selectivity of the sum of propylene glycol monoacetate and propylene glycol diacetate

TABLE 3

|  | First Reaction | 10th Reaction | 20th Reaction |
|---|---|---|---|
| Reaction Products (millimoles) |  |  |  |
| Propylene glycol monoacetate | 75.7 | 57.9 | 37.2 |
| Propylene glycol diacetate | 5.4 | 2.6 | 1.4 |
| Propionaldehyde and acetone | 11.8 | 9.2 | 2.4 |
| Conversion (%) | 96.3 | 72.3 | 42.5 |
| Selectivity (%)** | 87.3 | 86.8 | 94.1 |

Note:
**Same as in Table 2.

TABLE 4

|  | First Reaction | Second Reaction | Third Reaction |
|---|---|---|---|
| Reaction Products (millimoles) |  |  |  |
| Propylene glycol monoacetate | 78.8 | 23.3 | 3.1 |
| Propylene glycol diacetate | 4.5 | 6.0 | 0 |
| Propionaldehyde and acetone | 6.7 | 2.5 | 1.1 |
| Conversion (%) | 93.3 | 22.0 | 2.9 |
| Selectivity (%)** | 92.6 | 92.1 | 73.8 |

Note:
**Same as in Table 2.

TABLE 5

|  | EXAMPLE 3 | EXAMPLE 4 |
|---|---|---|
| Reaction Products (millimoles) |  |  |
| Propylene glycol monoacetate | 99.5 | 49.9 |
| Propylene glycol diacetate | 6.1 | 2.3 |
| Propionaldehyde and acetone | 33.9 | 16.2 |
| Selectivity (%)** | 75.7 | 76.3 |

Note:
**Same as in Table 2.

TABLE 6

|  | EXAMPLE | | | | | |
|---|---|---|---|---|---|---|
|  | 5 | 6 | 7 | 8 | 9 | 10 |
| Metal Halide |  |  |  |  |  |  |
| M Cl$_n$ | NaCl | CuCl$_2$ | ZnCl$_2$ | SbCl$_3$ | MnCl$_2$ | BiCl$_3$ |
| millimoles | 2 | 1 | 1 | 0.67 | 1 | 0.67 |
| Reaction Products (millimoles) |  |  |  |  |  |  |
| Propylene glycol monoacetate | 57.6 | 67.0 | 66.8 | 61.2 | 45.2 | 83.2 |
| Propylene glycol diacetate | 5.6 | 4.8 | 5.6 | 7.2 | 4.2 | 8.4 |

What is claimed is:

1. A process for producing glycol monoesters using a catalyst which is regenerated, comprising
   (a) reacting at least one carboxylic acid selected from the group consisting of acetic acid, propionic acid, butyric acid and isobutyric acid; at least one olefin selected from the group consisting of ethylene, propylene, butene-1, butene-2, cyclopentene and cyclohexene; and oxygen, in the presence of said catalyst containing (A) a palladium component, (B) an oxygen-containing nitrogen compound, and (C) a metal halide as major constituents, wherein the molar ratio of the oxygen-containing nitrogen compound (B) to the palladium component (A) is from 0.5 to less than 2.0 and the elemental ratio of the halogen atom in the metal halide (C) to the palladium atom in the palladium component (A) is at least 1, to produce glycol monoester; and
   (b) regenerating said catalyst by reduction with hydrogen and reusing the catalyst for step (a) reaction to produce glycol monoester.

2. The process as claimed in claim 1, wherein the elemental ratio of the halogen atom in the metal halide (C) to the palladium atom in the palladium component (A) is from 1 to 3.

3. The process as claimed in claim 2, wherein the metal halide (C) is at least one compound selected from the group consisting of lithium chloride, sodium chloride, copper chloride, manganese chloride, zinc chloride, cobalt chloride, bismuth chloride and antimony chloride.

4. The process as claimed in claim 2, wherein the oxygen-containing nitrogen compound (B) is at least one compound selected from the group consisting of nitric acid, nitrogen monoxide, nitrogen dioxide, nitrous acid esters, nitric acid salts, and nitrous acid salts.

5. The process as claimed in claim 1, wherein the palladium component (A) is at least one component selected from the group consisting of metallic palladium, palladium salt and palladium oxide.

6. The process as claimed in claim 5, wherein the palladium component (A) is metallic palladium.

7. The process as claimed in claim 1, wherein the oxygen-containing nitrogen compound (B) is at least one compound selected from the group consisting of nitric acid, nitrogen monoxide, nitrogen dioxide, nitrous acid esters, nitric acid salts, and nitrous acid salts.

8. The process as claimed in claim 1, wherein the carboxylic acid is acetic acid.

9. The process as claimed in claim 1, wherein the olefin is ethylene or propylene.

10. The process as claimed in claim 1, wherein the oxygen-containing nitrogen compound (B) is lithium nitrate or normal butyl nitrite.

11. The process of claim 1 wherein the catalyst is regenerated and reused two times.

12. The process of claim 1 wherein the catalyst is regenerated and reused three times.

13. The process of claim 1 wherein the catalyst is regenerated and reused ten times.

14. The process of claim 1 wherein the catalyst is regenerated and reused fifteen times.

15. The process of claim 1 wherein the catalyst is regenerated and reused twenty times.

16. The process of claim 1 wherein the catalyst is regenerated and reused thirty times.

17. The process as claimed in claim 1, wherein the metal halide (C) is at least one compound selected from the group consisting of lithium chloride, sodium chloride, copper chloride, manganese chloride, zinc chloride, cobalt chloride, bismuth chloride and antimony chloride.

18. The process as claimed in claim 17, wherein the oxygen-containing nitrogen compound (B) is at least one compound selected from the group consisting of nitric acid, nitrogen monoxide, nitrogen dioxide, nitrous acid esters, nitric acid salts, and nitrous acid salts.

19. The process as claimed in claim 18, wherein the palladium compound (A) is at least one component selected from the group consisting of metallic palladium, palladium salt and palladium oxide.

20. The process as claimed in claim 19, wherein the oxygen-containing nitrogen compound (B) as lithium nitrate or normal butyl nitrite.

21. The process as claimed in claim 20, wherein the carboxylic acid is acetic acid.

22. The process as claimed in claim 21, wherein the olefin is ethylene.

23. The process as claimed in claim 21, wherein the olefin is propylene.

24. The process of claim 21, wherein the olefin is ethylene or propylene and wherein the metal halide is sodium chloride.

25. The process of claim 21, wherein the olefin is ethylene or propylene and wherein the metal halide is copper chloride.

26. The process of claim 21, wherein the olefin is ethylene or propylene and wherein the metal halide is antimony chloride.

* * * * *